United States Patent [19]

Kasuya et al.

[11] Patent Number: 5,013,660
[45] Date of Patent: May 7, 1991

[54] METHOD OF IMPLANTING LIVING CELLS WITH A FOREIGN SUBSTANCE

[75] Inventors: Takahiro Kasuya; Yoji Ikawa; Motowo Tsukakoshi, all of Wako; Shunichi Kurata, Fuchu, all of Japan

[73] Assignee: Science and Technology Agency, Tokyo, Japan

[21] Appl. No.: 579,176

[22] Filed: Sep. 5, 1990

Related U.S. Application Data

[63] Continuation of Ser. No. 185,243, Apr. 19, 1988, abandoned, which is a continuation of Ser. No. 660,376, Oct. 12, 1984, abandoned.

[30] Foreign Application Priority Data

Oct. 13, 1983 [JP] Japan .................. 58-191379

[51] Int. Cl.[5] .............. C12N 13/00; C12N 5/10; C12N 5/04; C12N 5/06
[52] U.S. Cl. ................... 435/173; 435/240.1; 435/240.2; 435/240.4; 435/172.3; 435/254; 435/255; 435/256; 935/52
[58] Field of Search ............ 435/173, 240.1, 240.2, 435/240.4; 935/52

[56] References Cited

U.S. PATENT DOCUMENTS 4,071,657  1/1978  Dittrich et al. ............. 219/121.69
4,302,670  11/1981 Zaderej ........................ 935/92
4,338,397  7/1982  Gilbert .......................... 435/68

FOREIGN PATENT DOCUMENTS 2224902  10/1974 France .
58-76091  5/1983  Japan .
8204443  12/1982 PCT Int'l Appl. ............. 935/53

OTHER PUBLICATIONS

Loyter, A. et al., Proc. Natl. Acad. Sci. USA 79:422-426 (1-1982).
Kurata, S. et al., Reza Kagaku Kenkyu, 6:37-40 (1984) cited in Chemical Abstract CA 102(17):144133t.
Tsukakoshi, M. et al, Appl. Phys. B., B35(3):134-140 (1984) cited in Chemical Abstract CA 102(3):20715q.
Zimmermann, Biochem Biophys Acta, 694, 1982, pp. 227-277, "Electric Field Mediated Fusion and Related Electrical Phenomena".
F. L. Graham and A. J. Van Der Eb, "A New Technique for the Assay of Infectivity of Human Adenovirus 5 DNA", 1973, Virology, pp. 456-467.
Geoffrey M. Cooper, Sharon Okenquist & Laren Silverman, "Transforming Activity of DNA of Chemically Transformed and Normal Cells" 1980 Nature, vol. 284, pp. 418-421.
Mario R. Capecchi, "High Efficiency Transformation by Direct Microinjection of DNA into Cultured Mammalian Cells", 1980, Cell, vol. 22, pp. 479-488.
Elaine G. Diacumakos, Scott Holland, and Pauline Pecora, "A Microsurgical Methodology for Human Cells in Vitro: Evolution and Applications", Apr., 1970, Proceedings of the N.A. of Sciences, vol. 65, No. 4, pp. 911-918.
Fumiichiro Yamamoto, Mitsuru Furusawa, Iwao Furusawa and Masuo Obinata, "The 'Pricking' Method (A New Efficient Technique for Mechanically Introducing Foreign DNA into the Nuclei of Culture Cells", 1982, Experimental Cell Research 142, pp. 79-84.

(List continued on next page.)

Primary Examiner—Elizabeth C. Weimar
Assistant Examiner—George C. Elliott
Attorney, Agent, or Firm—Brumbaugh, Graves, Donohue & Raymond

[57] ABSTRACT

Disclosed is a method and apparatus implanting living cells with a foreign substance with the aid of laser beams. According to this invention living cells are exposed to a laser microbeam of energy sufficient to modify a selected part of the cell to be temporarily transparent to a foreign substance. After the foreign substance gets in the host cell, the selected part of the cell recovers to the original state, thereby confining the foreign substance in the cell.

9 Claims, 9 Drawing Sheets

10μ

10μ

FIG.2
(A)
(B)
(C)

10μ

METHOD OF IMPLANTING LIVING CELLS WITH A FOREIGN SUBSTANCE

This application is a continuation of application Ser. No. 185,243, filed on Apr. 19, 1988, which in turn, is a continuation of application of Ser. No. 660,376 filed Oct. 12, 1984, both of which are now abandoned.

FIELD OF THE INVENTION

This invention relates to a method of incorporating a foreign substance into living cells.

BACKGROUND OF THE INVENTION

In the field of analysis of gene expression the behavior of those genes which determine the character of a living thing can be studied by incorporating selected genes into living cells and by examining the transformation of the cells having added genetic material. For example, DNA can be extracted from cancerous cells, and divided into minute fragments of different sizes. These fragments are classified in terms of size, and fragments of different size are incorporated into living cells. As a result of such incorporation, some of the cells are found to be cancerous, presumably as a result of incorporation of the foreign DNA fragments. By this technique, cancer-associated fragments can then be identified in terms of size.

A prior art implantation method comprises the steps of: putting living cells in a solution containing DNA fragments; making a small hole in each living cell with the aid of a fine needle under an optical microscope; allowing DNA fragments to enter the cells through the hole; and confining the fragments in the cell when the hole in the cell heals (See Japanese Patent Application No. 56-171347, disclosed as Public Disclosure Number 58-76091 on May 9, 1983). Another prior art implantation method comprises the steps of: precipitating DNA using calcium phosphate in a culture medium; and making use of the phagocytosis of living cells to incorporate the precipitated DNA into the living cells.

The prior art implantation methods, however, are not entirely satisfactory. The former implantation method requires skilled manipulation of the needle. Otherwise, no holes can be made without injuring the living cells. Also the work is tedious and laborious although the implantation succeeds at a relatively high rate. Furthermore, it is impossible to make holes in certain cells, regardless of the type of needle used.

The latter implantation method is capable of handling a great number of cells at one time. The success rate for incorporation of DNA fragments into host cells by this method, however, is very low, say one in ten thousand (1/10,000) at best. Thus, the rate at which the character of the implanted cells is transformed is very small, and accordingly a very large number of cells need to be implanted with DNA fractions. This demand cannot be met. Also, disadvantageously the method requires addition of calcium phosphate of so high a concentration that the additive tends to injure living cells.

SUMMARY OF THE INVENTION

The inventors have found that a living cell when exposed to a laser of appropriate energy is partly and temporarily modified to be permeable to a foreign substance, thereby allowing the substance to enter the living cell and confining the same in the living cell upon recovery to the original condition. This invention is based on that discovery.

One object of this invention is to provide a method of implanting a very large number of cells with a foreign substance such as DNA with maximum possible efficiency.

Another object of this invention is to provide a method for implanting a very large number of cells with a foreign substance such as DNA in the minimum possible time.

Still another object of this invention is to provide a method for making living cells temporarily permeable to a foreign substance without the necessity of subjecting living cells to a special treatment.

To attain these objects an implantation method according to this invention comprises the steps of: exposing each living cell to a fine laser beam such that at least a part of the cell surface becomes permeable to a foreign substance such as DNA, protein or any other biopolymer whereby the foreign substance is able to enter the host cell; and allowing the partially and temporarily modified living cells to encounter fragments of the foreign substance suspended in a medium, thereby allowing some of the fragments to enter to cells.

A laser beam has good directionality, and can be focused to a spot of minimal diameter using an optical microscope. These properties make it possible to use a laser beam to make a minute "hole" (submicron in diameter) in a host cell. (The word "hole" is intended to mean that the area of a living cell which is made permeable to a foreign substance resembles a hole.) A pulse laser beam can be used, in which case the temperature rise of the cell due to exposure to the laser beam can be advantageously suppressed by reducing the pulse duration of the laser. This prevents the cell from being thermally killed.

Lasers produce monochromatic irradiation. In accordance with the invention, the wavelength of this irradiation can be selected as appropriate for the purpose of making "holes" in a given type host cell, considering the optical characteristics of the cell wall and the cell membrane as well as the characteristics of a foreign substance to be incorporated.

The strength of a laser also can be adjusted over a wide range using appropriate electric control. The focusing depth in the host cell can be easily controlled with appropriate optical means. These together provide a great advantage to the microsurgery to which this invention is to be applied. An apparatus for making "holes" in living cells according to this invention uses a laser microbeam appropriate for the purpose of conducting a microsurgery on a living cell without injuring its self-healing capability.

The length of time for which cells are exposed to a laser microbeam should be controlled so as to be long enough to make "holes" in the cells, but not enough to thermally kill the cells. The exposure time can be controlled by using a train of laser pulses each having a duration controlled appropriately for the purpose, or by scanning with a laser microbeam in an appropriate length of time a field in which a large number of living cells are suspended in a solution. Also, a laser microbeam can be directed to selected portions of a single cell selected from among those cells floating in a solution.

Thus, according to one aspect of this invention an apparatus for making "holes" in living cells comprises: a laser source for providing a pulse or continuous wave laser microbeam, an optical system for projecting a laser microbeam on to living cells, and means for monitoring living suspended cells in a solution. According to another aspect of this invention a microsurgery apparatus comprises: a laser source, an optical system for projecting a laser microbeam on to living cells, means for monitoring living cells suspended in a solution, means for determining the position of a cell selected among those appearing in the field of said monitoring means, and means responsive to a start signal from said positions determining means for controlling the supply of the laser light from said laser system.

According to still another aspect of this invention a microsurgery apparatus comprises: a laser source, an optical system for projecting a laser microbeam on to living cells, means for monitoring living cells suspended in a solution, means for determining the position of a cell selected among those appearing in the field of said monitoring means, means responsive to cell position signals from said position determining means for storing, and means for controlling the laser microbeam and directing the same to selected cells one after another.

BRIEF DESCRIPTION OF THE DRAWINGS

FIG. 2 shows a sequence of microscopic photographs showing the formation of a hole in an NRK cell using a laser microbeam and the subsequent healing of the hole;

DESCRIPTION OF PREFERRED EMBODIMENTS

As described earlier, the implantation method according to this invention comprises the steps of exposing living host cells to a laser microbeam to make the surface of the host cells temporarily permeable to a foreign substance, i.e. to make "holes" in the host cells, and allowing these permeable cells to meet with fragments of a foreign substance, such that the foreign substance enters at least some of the permeable cells before these cells heal their holes, and confining the foreign substance in the host cells when the holes close.

There are a variety of modes in which fragments of a foreign substance can meet with permeable host cells and enter the cell through the holes. For example, cells and fragments of the foreign substance are suspended together in a solution, and the cells are exposed to a laser microbeam one after another, thus causing permeable cells to coexist with the fragments in the solution. In a second approach, a solution containing host cells is supplied in drops to another solution containing fragments of a foreign substance, and each drop on the way to the lower solution is exposed and punched by a laser microbeam. Third, a liquid carrying host cells and fragments of a foreign substance is made to flow across the field of a pulse or continuous wave laser. This final mode is most appropriate for the purpose of handling a large number of host cells.

EXAMPLE 1

Figure 1:
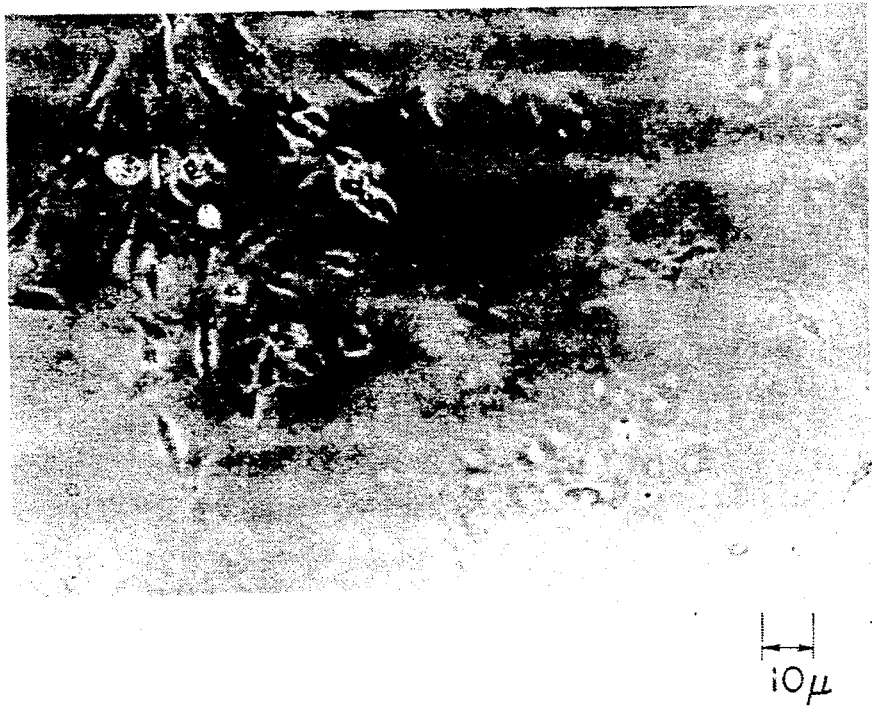
FIG. 1 is a copy of microscopic photograph showing NRK cells planted with gene (Ecogpt) according to this invention.

Referring to FIG. 1, living cells implanted with fragments of a foreign substance and dead cells which could not survive owing to there being no foreign substance implanted therein are shown under microscope. NRK cells originating from the kidney of an Osborn Mendel rat were modified so as to be unable to survive without Ecogpt (Xanthine-guanine Phosphoribosyl Transferase) being incorporated therein, and the NRK cells thus modified were put in an Ecogpt-containing medium (DMEM added with 10-percent unborn calf's blood serum). An infrared beam ($\lambda=1.06$ microns) from a laser device (YAG laser) was converted to an ultraviolet beam ($\lambda=355$ nanometers), and the ultraviolet beam was introduced into a laser microscope. Then, living cells floating in the medium in the field of the microscope were exposed to pulsed laser beam irradiation having a pulse duration of 10 nanoseconds. The laser beam was applied to the cells in one half of the field at the rate of ten pulses per second, and a large number of living cells were treated.

The results are shown in FIG. 1 where cells which were exposed to the laser (left half) are alive, while those that were not exposed to the laser (right half) are dead. The cells exposed to the laser took up Ecogpt fragments of the foreign substance and therefore survived, but the cells that were not exposed to the laser could not take up Ecogpt fragments, and therefore died.

EXAMPLE 2

Living cells can heal and close their holes essentially immediately after being made. FIG. 2 is a photograph of a video sight showing NRK cell immediately after being punched by a laser microbeam. Specifically, FIG. 2(A) shows the appearance of cells at the instant they were punched. FIG. 2(B) shows the appearance of cells immediately after being punched, and there is already a decrease in the size of the hole. FIG. 2(C) shows the appearance of cells after healing of the hole.

EXAMPLE 3

Figure 3:
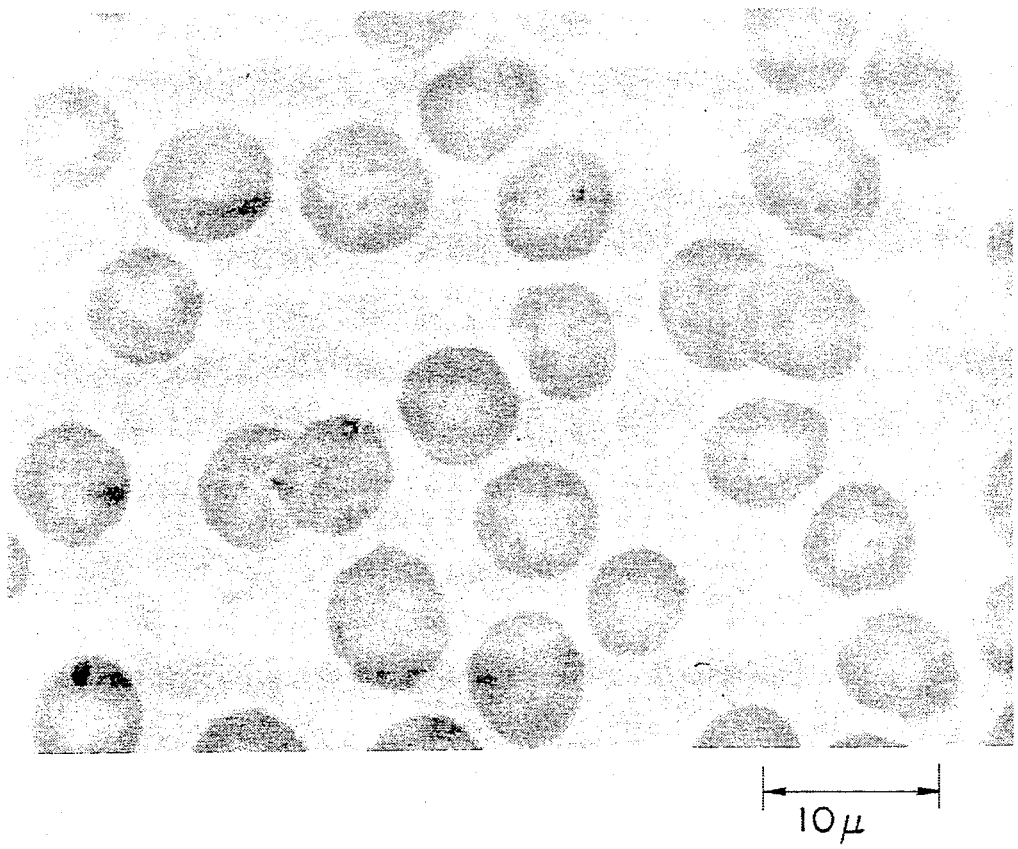
FIG. 3 is a copy of microscopic photograph showing punched cells (human red blood cells)

FIG. 3 shows human blood cells which have been dyed and punched with a laser microbeam. These photographs show the appearance of living cells immediately after being punched, proving that a single cell can be punched at selected portions as a result of the good controllability of laser beams. As is apparent from the above, the method of this invention permits punching for the sake of implantation of a foreign substance in the cell. Also, this invention can be equally applied to microsurgery of cells, as for instance breaking a particular minute organ in a single cell.

Application of this invention to the incorporation of genes into cells permits: production of useful substances in cells (for instance, synthesis of insulin or any other useful human substance within living cells); and improvement of domestic animals and agricultural products (by substituting different genes for each other in different kinds of plants; or by incorporating good genes without recourse to fertilization).

A cell-punching apparatus for performing the method of this invention is described with reference to FIG. 4.

A laser beam ($\lambda = 1060$ nm) for punching living cells is generated by a laser source 1 and passes through a frequency multiplier 3 essentially composed of KDP or any other crystal which is appropriate for the purpose of converting the infrared light to ultraviolet ($\lambda = 355$ nm or 265 nm). The ultraviolet laser beam passes through a shutter which is controlled by an associated shutter driver 4. Then, the laser beam 2 is shaped by a beam shaper 6. The laser beam thus shaped is directed toward a microscope-and-beam combiner 8 by reflector 7. A reference laser beam 10 functioning as a pilot or tracing beam (for instance, He-Ne laser $\lambda = 633$ nm) is generated by a visible laser source 9. The reference laser 10 is shaped by a beam shaper 11, and then the shaped laser beam is reflected by a reflector 12 to travel toward the beam combiner 8 along with the punching laser beam 2. The punching and reference laser beams 2 and 10 after passing through a beam deflector 13 are combined by a condenser lens 8′. The combined laser beam strikes cells floating in a solution in which fragments of a foreign substance such as DNA are suspended. When cells are exposed to the laser beam, the cells are punched and become permeable to the fragments. A sample holder 15 is illuminated by a lamp 16 under the holder, thereby projecting an image of the cells in the sample holder to a TV camera 17 through the condenser lens 8′, and producing a visible image of cell distribution on a TV monitor 18. A stage 14 carrying the sample holder 15 is composed of an X-Y stage which is driven by a stepping motor 20.

When shutter 5 is closed, the punching laser beam does not reach the sample holder 15, and the visible laser beam 10 from the laser source 9 functions as a pilot beam, thus indicating the place where the punching laser beam will strike. When the shutter 5 is open, the visible laser beam 10 is combined with the punching laser beam 2 and functions as a tracing beam, thus making visible the trace on which the punching laser beam travels.

In punching cells, the stage 14 is driven until the image of a congregation of cells appears in the field of the monitor 18. Then the shutter 5 is kept open, thereby permitting the continuous irradiation of the sample holder 15 by the punching laser beam 2. Cells are exposed to the punching laser beam 2 one after another simply by moving the stage 14. Fragments of a foreign substance floating in the vicinity of punched cells enter the cells via the "holes" in these punched cells. The living cells heal their holes in a few seconds, thus confining the foreign substance in the cells. As a result the healed cells may now carry a particular gene present in the fragments of foreign substance.

Moving the sample holder with respect to the stationary pulse or continuous wave laser beam causes the laser beam to sweep the cell-floating area in the solution. This is most effective to treat a lot of cells within a relatively short time.

Figure 5:
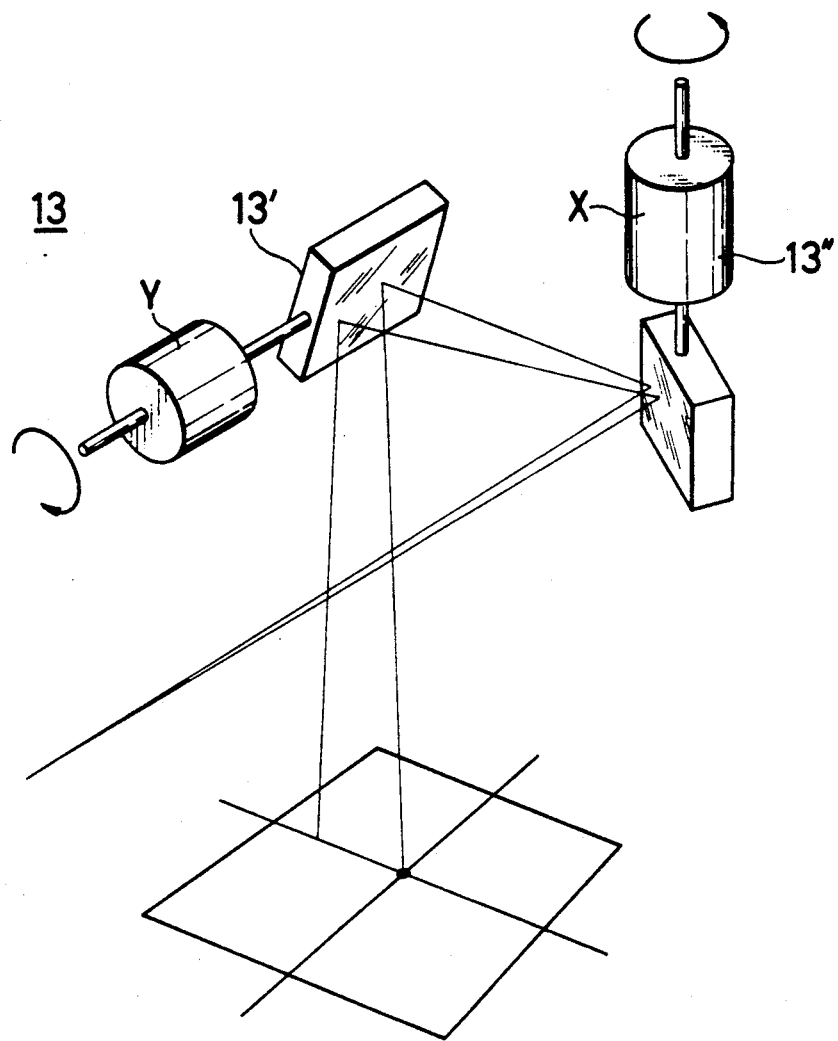
FIG. 5 is a perspective view of a laser microbeam deflector used in the laser punching apparatus of FIG. 4.
Figure 10:
FIG. 10 is a copy of microscopic photograph showing details of portions of cells swept by a laser microbeam.

FIG. 5 shows a laser deflector 13 as comprising a combination of two galvanometers 13′ and 13″ each equipped with a reflector. The laser deflector 13 is driven by an associated two-dimensional scanning control 38 so as to cause the visible laser beam 10 to scan a selected small area in the field of the sample holder. Then, resultant reflected rays, luminescence rays and scattered rays fall on the TV camera or a still camera after passing through the condenser 8′, thus producing a clear image showing, in detail, the inner structures of selected cells. FIG. 10 is a copy of microscopic photograph taken by sweeping with the visible laser beam, showing human red blood cells.

The area encircled with a white line is the one swept by the visible laser beam 10, showing details of the inner structures of selected human red blood cells, in contrast with the rest area of the photograph illuminated by the lamp 16. Although the reason for providing such a clear detailed image of the inner structure of the cell is not known, it appears to the inventors that the laser after passing through the condenser lens focuses on a point at a determined depth, thereby causing the appearance of a clear image of the inner structure of the cell taken along the focal plane at the depth. Thus the cell punching apparatus equipped with a laser sweeping with permits the monitoring of modification of the inner structure of a cell punched and implanted with a foreign substance.

Figure 6:
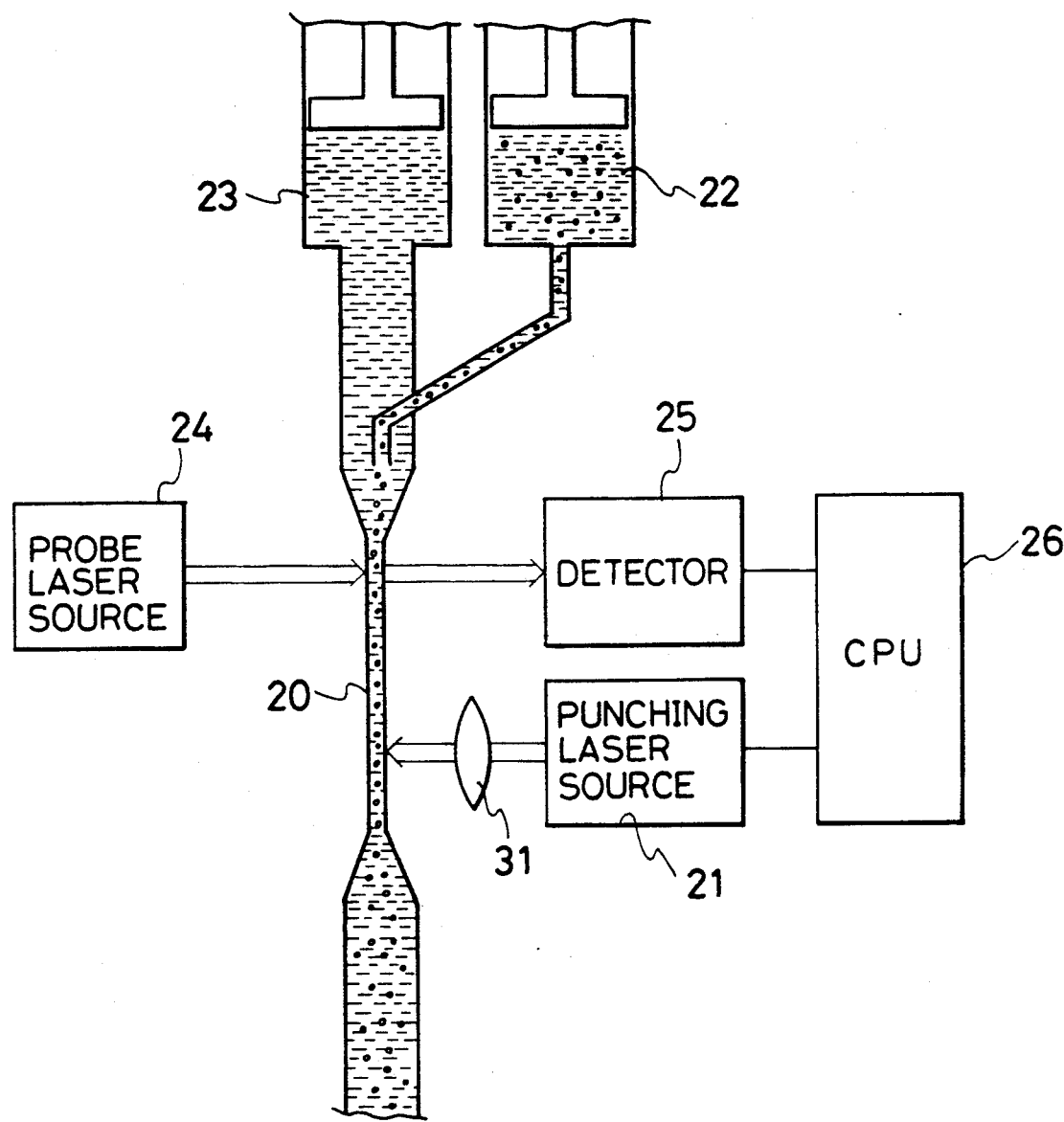
FIG. 6 is a schematic block diagram of a laser punching apparatus according to a second embodiment of this invention.

FIG. 6 shows a second cell punching apparatus useful in the method of this invention. As shown, cells descend one after another in a fine transparent tube 20 so that they are exposed to the punching laser beam from a laser source 21. Specifically, a solution 22 containing living cells and a protection liquid such as physiological saline 23 are fed to the fine tube 20. A probe laser beam is emitted by a probe laser source 24 to a detector 25, and passes through the, descending flow upstream of the place at which cells are exposed to the punching laser beam. The detector 25 detects a cell passing by the detector to generate and send a detection signal to a central processing unit 26, and then the central processing unit 26 times the start of the punching laser source 21, thus causing the punching beam to hit the descending cell to make a hole therein. Fragments of a foreign substance to be incorporated in cells such as DNA may be put in the solution 22 or the physiological saline 23. Thus, the cell punching apparatus can punch about 1000 cells per second. If use is made of a detector capable of determining the angle of diffusion over which the laser beam spreads when falling on a cell, cells can be classified in terms of size, and hence kind. Thus, it is possible to select and punch a particular kind of cells among different ones in a solution 22. The casting of the punching laser beam on cells may be controlled by controlling a shutter (not shown) provided between the fine tube 20 and the laser source 21 rather than by controlling the punching laser source 21.

Figure 7:
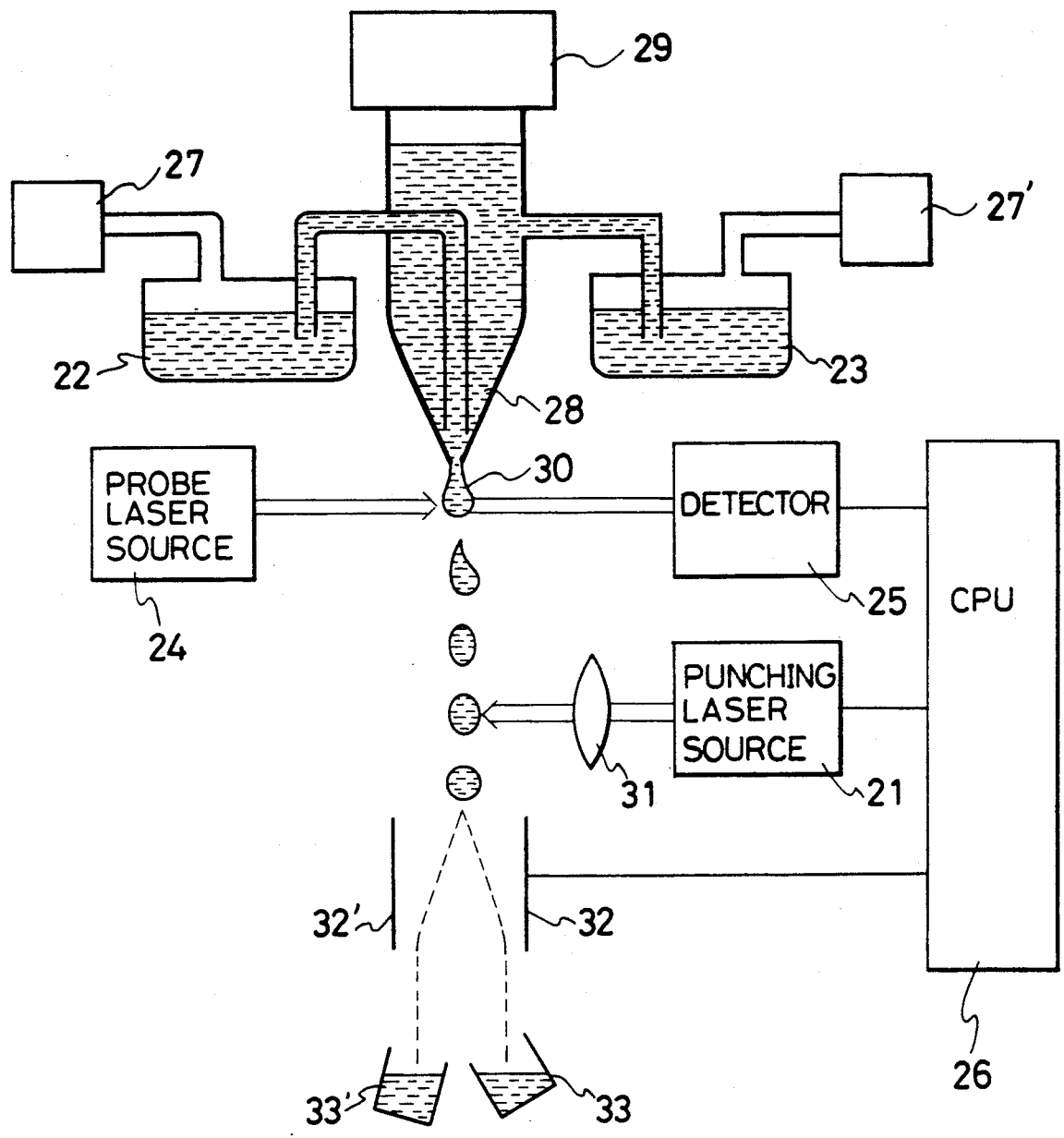
FIG. 7 is a schematic block diagram of a laser punching apparatus according to a third embodiment of this invention.

FIG. 7 shows a third cell-punching apparatus useful in the invention. This apparatus is so designed that a solution containing living cells is supplied in drops across the punching laser beam. Specifically, a suspension 22 containing living cells, and a protection liquid 23 such as physiological saline are fed to a nozzle 28 under pressure by air pumps 27 and 27′. A mixture of suspension and protection liquid falls in drops 30 under the action of a supersonic nozzle vibrator 29, which may be composed of, for instance, a piezoelectric element. In operation, the fall of a drop 30 is detected by a probe laser falling on a detector 25, and then the detector 25 sends a detection signal to a central processing unit 26.

The central processing unit 26 signals a punching laser source 21 to emit a punching laser beam at the instant the drop is about to cross the punching laser source 21, thereby making holes in sells in the drop.

When drops 30 are exposed to the probe laser, it is possible to determine which kind (or size) of cells are contained in each drop with the aid of a conventional laser analyzing system, and if drops are charged with electricity of which the polarity and/or quality varies with the kind of the cell, and if these drops fall across the electric field between opposite electrodes 32 and 32', they will be classified in terms of the polarity and/or quantity of the electric charge, and will be put in different receptacles 33 33', thus classifying punched cells in terms of kind.

As an alternative, if the drops are charged with electricity of the same sign and quantity, the strength of the electric field may be varied with the kind of the punched cells. Fragments of a foreign substance to be incorporated into cells may be put in the suspension 22, the protection liquid 23 or in the receptacles 33 and 33'. The casting of a punching laser beam from the punching laser source 21 may be controlled by controlling a shutter (not shown) provided between the path of drops and the punching laser source 21 rather than by controlling the laser source 21. In some instances the continuous casting of the punching laser beam may be preferred.

Figure 8:
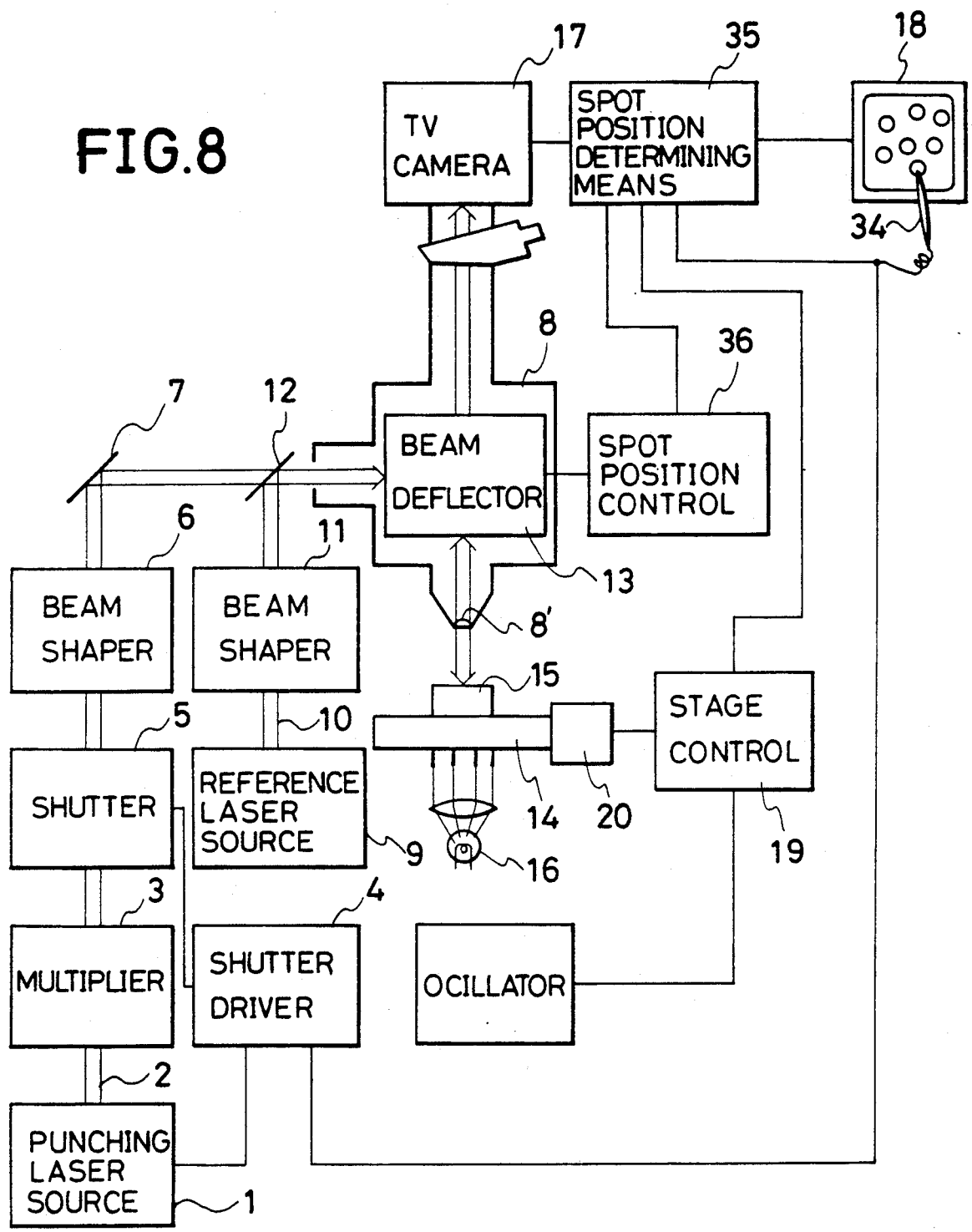
FIG. 8 is a schematic block diagram of a laser punching apparatus according to a fourth embodiment of this invention.

FIG. 8 shows a fourth cell punching apparatus useful in the invention.

Figure 4:
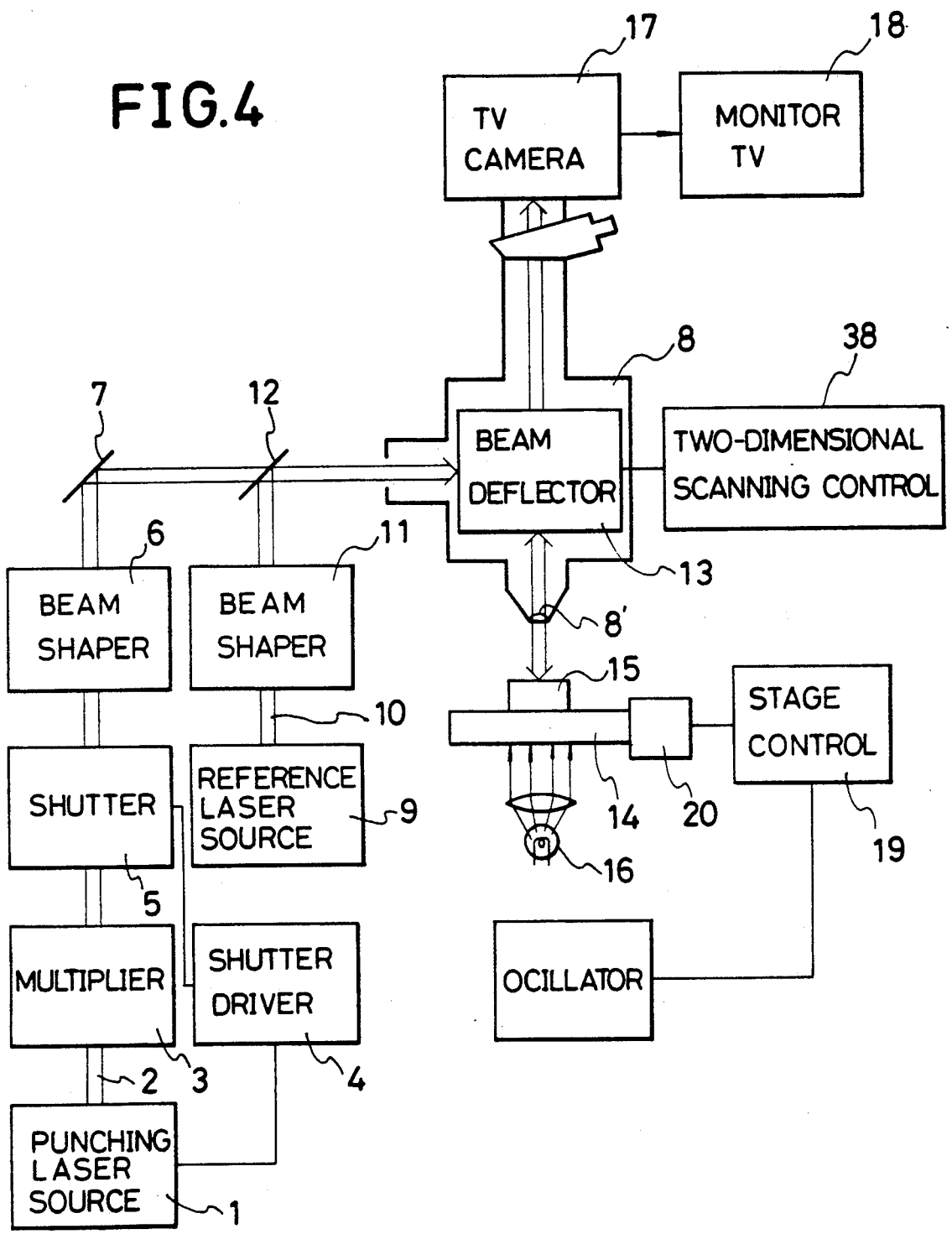
FIG. 4 is a schematic block diagram of a laser punching apparatus according to a first embodiment of this invention.

The cell punching apparatus of FIG. 8 is different from that of FIG. 4 in that the former is equipped with a light pen 34 for indicating cells appearing in the field of the TV monitor 18, an associated spot position determining means 35 for determining the coordinates of point of the monitor field on which the light pen is put and a spot position control 36 for controlling the laser deflector 13 so as to direct the laser beam to the same point as the light pen indicates. The spot position control 36 is responsive to a coordinate signal from the spot position determining means 35 for driving the laser deflector 13 to direct the laser beam to the position indicated by the light pen. In operation, the distribution of living cells in the sample holder 15 is watched by the TV monitor 18, and the light pen 34 is put on a selected part of a desired living cell selected among those appearing in the field of the TV monitor 18. The coordinate of the point indicated by the light pen 34 is determined by the spot position determining means 35. A position signal representing the position indicated by the light pen is directed form the spot position determining means 35 to the spot position control 36. Then, the spot position control 36 drives the laser deflector 13 to direct the laser beams 2 and 10 to the point indicated by the light pen 34.

At the same time as the light pen indicates a given position, the position determining means generates a start signal, and the shutter driver 4 is responsive to the start signal for opening the shutter 5 for a predetermined period. Thus, a corresponding number of laser pulses 2 are thrown onto the point indicated by the light pen 34. The punched cell allows fragments of a foreign substance to get therein, and then the cell heals its hole to confine the fragment therein as described earlier.

In this particular embodiment the spot position control 36 is used to drive the laser deflector 13 for throwing the laser beam to a given position. As an alternative the stage position control 19 is used to drive the stage 14 to attain the same effect.

Figure 9:
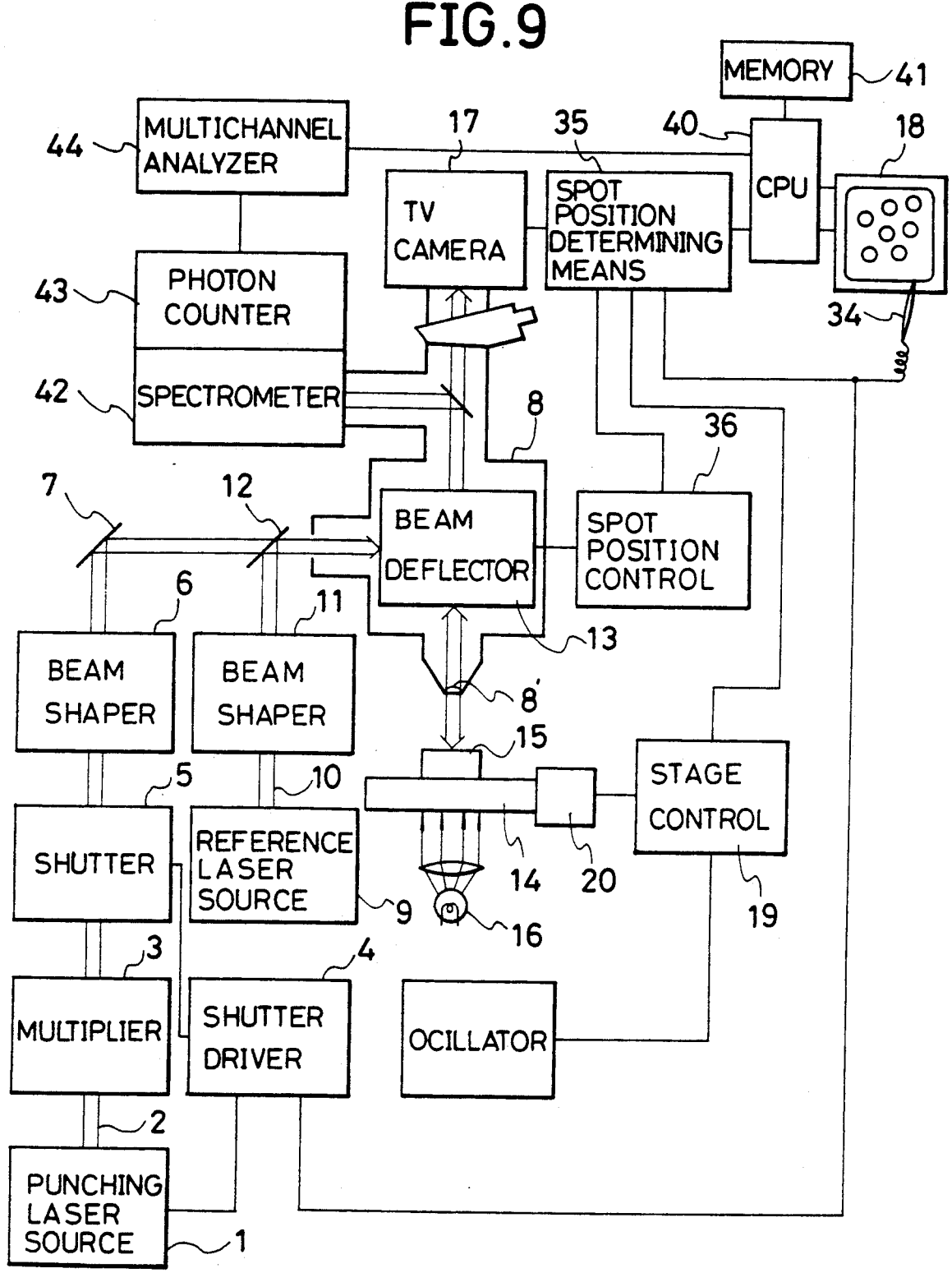
FIG. 9 is a schematic block diagram of a laser punching apparatus according to a fifth embodiment of this invention.

FIG. 9 shows a fifth cell punching apparatus useful in the invention.

A light pen 34 is used to indicate selected point or points on each of selected cells or every cell appearing in the field of a TV monitor 18, and a spot position determining means 35 determines the coordinates of the points indicated by the light pen 34. Then, signals representing these coordinates are directed to memory 41 through a central processing unit 40 so that the coordinates of the points indicated by the light pen are stored in the memory 41. These coordinates are read out one after another to input in the spot position control 36 under the control of the central processing unit 40. The spot position control 36 controls the laser defector 13 in the same way as the cell punching apparatus of the fourth embodiment. On the other hand, the central processing unit 40 directs a drive signal to the shutter driver 4, thereby opening the shutter 5 for a predetermined period to throw a punching laser beam 2 to the points indicated by the light pen one after another. Thanks to the use of memory, living cells appearing in the field of the TV monitor are punched in rapid succession. It is possible to make a decision as to whether a cell is present or not in terms of the amplitude of video-signal from the TV camera 17, and if the spot position detector 35 is designed to make such a decision, the cell punching will be completely automated. Specifically, the so designed spot position detector 35 may analyze video signals from the TV camera 17, thereby determining the positions of cells appearing in the field of the TV camera, and then the position signals representing the positions of cells are directed to the memory 41 for storing. In this case a pattern identification means may be used to identify cells in terms of the contour of cell.

As shown in FIG. 9, a spectrometer 42, a photon-counter 43 and a multichannel analyzer 44 together constitute an analyzing system, which may be used as a monitor. Specifically, the optical system can make a decision as to whether a cell is present or not at a given coordinate (and in some instances a decision as to whether a cell core is present or absent at a given coordinate), in terms of spectrographic characteristics.

The embodiments described above use two different laser sources, that is, a punching laser source and reference laser source. It, however, should be noted that if a continuous or non-pulse visible laser beam is used as a punching one, no reference laser beam is necessary because the spot on which the punching beam focuses is visible in the field of a TV monitor. Also, it should be noted that a shutter for controlling the throwing of the punching laser beam is not limited to the mechanical one, and that a conventional photo-switch may be used for the purpose. The expression, "fragments or fractions of a foreign substance" used herein is intended to include virus, every kind of protein, and full genome of DNA.

Finally, in the examples and embodiments described herein above, selected portion or portions of each living cell are modified when exposed to a laser beam. This should not be understood a limitative. Indeed, the whole area of the living cell may be modified if use is made of a laser beam larger in diameter than the living cell, indeed.

We claim:

1. Method of introducing a foreign substance into living eukaryotic cells comprising exposing a suspension of living eukaryotic cells in a liquid medium to a laser beam whereby at least some of said living eukaryotic cells become temporarily permeable to said foreign substance, and adding the foreign substance to the liquid medium before or after said exposure, whereby said temporarily permeable eukaryotic cells are associated with said foreign substance so that said foreign substance can enter said temporarily permeable eukaryotic cells.

2. Method according to claim 1 wherein said laser beam is a continuous wave laser.

3. Method according to claim 2 wherein said living eukaryotic cells are transported through the path of said continuous wave laser beam.

4. Method according to claim 2 wherein the living eukaryotic cells are exposed to the laser beam by sweeping said continuous wave laser beam across a predetermined area of the suspension after said living eukaryotic cells are brought into association with said foreign substance.

5. Method according to claim 2 wherein said liquid medium is a medium appropriate for the cultivation of said living eukaryotic cells.

6. Method according to claim 1, wherein said laser beam is a pulsed laser beam.

7. Method according to claim 1 wherein said foreign substance is genetic material.

8. Method according to claim 1 wherein the living cells are animal cells.

9. Method according to claim 1 wherein the living cells are plant cells.

* * * * *